United States Patent [19]

Madrange nee Dermain et al.

[11] 4,403,070

[45] Sep. 6, 1983

[54] COSMETIC COMPOSITIONS FOR LACQUERS AND WAVE-SETTING LOTIONS, NEW COPOLYMERS AND PROCESS FOR PREPARING THEM

[76] Inventors: Annie Madrange nee Dermain, 4, rue du Prieuré, (78) Saint-Germain-en-Laye; Christos Papantoniou, 12, avenue Questroy, (93) Epinay-sur-Seine, both of France

[21] Appl. No.: 806

[22] Filed: Jan. 4, 1979

Related U.S. Application Data

[60] Continuation of Ser. No. 629,415, Nov. 6, 1975, abandoned, Division of Ser. No. 287,845, Sep. 11, 1972, Pat. No. 3,934,595.

[30] Foreign Application Priority Data

Sep. 13, 1971 [LU] Luxembourg ............................ 63896

[51] Int. Cl.³ .................. C08F 220/14; C08F 220/36; C08F 8/30; C08F 8/32
[52] U.S. Cl. .................................. 525/330.4; 424/47; 525/330.3; 526/212; 526/218; 526/312
[58] Field of Search ....................... 526/212, 218, 312; 525/329, 330.3, 330.4

[56] References Cited

U.S. PATENT DOCUMENTS 3,990,459 11/1976 Papantoniou ...................... 526/312
4,237,253 12/1980 Jacquet et al. ..................... 526/312

OTHER PUBLICATIONS

Billmeyer, J. Pol. Sci., Part C, No. 8, pp. 161–176, (1965).

Primary Examiner—Harry Wong, Jr.
Attorney, Agent, or Firm—Penrose Lucas Albright

[57] ABSTRACT

Copolymers having tertiary amine groups and composed of 16–43% methyl methacrylate, 25–54% dimethylamino ethyl methacrylate and 12–52% octadecyl methacrylate are particularly useful as hair treating resins with conventional carriers and additives. The copolymers can be crosslinked by up to 0.15 by an unsaturated agent to produce preferred copolymers used in wave-setting lotions in amounts of 1–3%. Such copolymers can also be partially or wholly quaternized by a quaternizing agent. Those copolymers not crosslinked are particularly useful as hair lacquers, especially in aerosol sprays in amounts of 1–4%. The molecular weight for the subject copolymers averages 10,000–1,500,000 and copolymerization can be effected in a solvent with a catalyst wherein the reaction mixture is heated for about 6 to 24 hours at about 80° C. When applied to the hair, the amount of lotion or lacquer used can be 10–100 c.c. and the treated hair is rolled. After treatment, the hair holds its shape well and is easy to comb.

6 Claims, No Drawings

COSMETIC COMPOSITIONS FOR LACQUERS AND WAVE-SETTING LOTIONS, NEW COPOLYMERS AND PROCESS FOR PREPARING THEM

This is a continuation of Ser. No. 629,415 filed Nov. 6, 1975, now abandoned, which is a division of application Ser. No. 287,845 filed Sept. 11, 1972, now Patent No. 3,934,595.

The present invention relates to new cosmetic compositions in the form of lacquers and wavesetting lotions which contain a copolymer possessing tertiary amine groups as the resin.

It has already been proposed to use copolymers possessing such tertiary amine groups in order to prepare lacquers or or wavesetting lotions.

In this field, the use of copolymers, and in particular of bipolymers, obtained by copolymerizing 10 to 90%, but preferably 15 to 90%, of an unsaturated ester possessing a tertiary amine group and 90 to 10%, but preferably 85 to 10%, of another unsaturated monomer, the tertiary amine groups of the copolymers being partially quaternised, have been recommended for producing such lacquers or wavesetting lotions.

It has been found, however, that these wavesetting lotions and lacquers based on such resins do not possess all the cosmetic characteristics which are generally required for such hair lotions and lacquers.

After extensive investigations, the applicants have found, entirely surprisingly, that, in order to obtain excellent lacquers and wavesetting lotions based on copolymers possessing tertiary amine groups, it was necessary to produce these copolymers using well defined proportions of each of the constituent monomers.

In effect, it has been found that on going outside the limits selected by the applicants, the cosmetic properties of the lacquers and wavesetting lotions were inferior.

Furthermore, these compositions make it possible to produce films which have an excellent shine and a good affinity for hair, which yields the double advantage of holding the head of hair better and of making it easier to comb, without destroying the copolymer film to any great extent.

In effect, it is well known that combing leads to practically complete removal of the resins used, which fall in the form of a white powder. In the case of the wavesetting lotions according to the invention, combing, as was stated above, is made possible, while the copolymer films can, nevertheless, be easily removed by brushing or by washing with a shampoo of conventional type.

It must be pointed out, moreover, that these lacquers and wavesetting lotions according to the invention make it possible for the hair to have a less greasy appearance and to look healthier. It was also found that the softness of the hair, after it had been dried, was markedly improved.

The subject of the present invention is a cosmetic composition for hair, in the form of lacquers or wavesetting lotions, characterized in that it contains, in a suitable cosmetic vehicle, at least one copolymer possessing tertiary amine groups, resulting from the copolymerization of 43 to 16% by weight of methyl methacrylate, 54 to 25% by weight of dimethylamino-ethyl methacrylate and 12 to 52% by weight of octadecyl methacrylate.

As has been stated above, these proportions of methyl methacrylate, dimethylamino-ethyl methacrylate and octadecyl methacrylate are of great importance if it is desired to obtain a film which possesses all the cosmetic properties mentioned above.

The copolymers according to the invention, which are completely soluble in absolute ethyl alcohol, are more particularly intended for preparing aerosol hair lacquers.

In a variant, the methyl methacrylate, dimethylaminoethyl methacrylate and octadecyl methacrylate terpolymers can be in a crosslinked form.

In general, this cross-linking is carried out during polymerization, for example by means of a small amount of ethylene glycol dimethacrylate or of any other crosslinking agent with a similar structure.

This quantity of crosslinking agent is generally not greater than 0.15 part of crosslinking agent per 100 parts of monomers.

Ethylene glycol dimethacrylate, which is preferably used as the crosslinking agent, possesses two unsaturated groups which simultaneously take part in the copolymerization in two chains of the copolymer, which has the result of producing crosslinking between the various chains of the copolymer.

These crosslinking bonds between the various chains of a copolymer by means of a molecule of ethylene glycol dimethacrylate can be represented in the following manner:

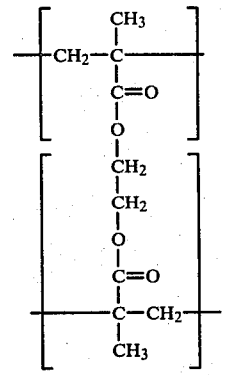

The crosslinked copolymers according to the invention are completely soluble in ethyl alcohol and are more particularly intended for preparing wavesetting lotions, while, on the other hand, the non-crosslinked copolymers are more particularly intended for preparing aerosol lacquers.

The crosslinked copolymers according to the invention can also be partially or completely quaternised, by means of at least one quaternising agent. This quaternisation can be carried out, for example, by means of agents such as dimethylsulphate and lower alkyl halides such as methyl iodide or ethyl bromide, and 2-bromo-ethanol. β-propiolactone, 1,3-propane-sulphone, hydrochloric acid and benzyl chloride, as well as by means of any other quaternising agent usually employed in this type agent usually employed in this type of reaction.

These crosslinked, quaternized copolymers, which are soluble in diluted alcohols, are more particularly intended for preparing wavesetting lotions, without however excluding the possibility of using them in hair lacquer formulations, especially suited to their solubility.

In general terms, the copolymers used according to the invention have a molecular weight which can be between about 10,000 and 1,500,000 (Light scattering method).

The wavesetting lotions according to the invention are in the form of aqueous or aqueous-alcholic solutions which contain 20 to 70% of alcohol, and have a copolymer concentration of between 1 and 3%.

The alcohols which are generally used for producing such wavesetting lotions are preferably lower aliphatic alcohols, of low molecular weight, such as ethanol or isopropanol.

The hair lacquers according to the invention are produced by dissolving at least one copolymer as defined above in an alcohol, this solution being placed in an aerosol vessel and mixed with a propellant gas liquefied under pressure.

It is possible, for example, to produce an aerosol lacquer according to the invention by adding 1 to 4% by weight of at least one copolymer as described above to a mixture consisting of ¼ to ⅓ of an anhydrous aliphatic alcohol such as ethanol or isopropanol and ¾ to ⅔ of a liquefied propellant gas or of a mixture of liquefied propellant gases such as halogenated hydrocarbons of the trichlorofluoromethane or dichlorodifluoromethane type.

Of course, it is possible to add adjuvants, such as plasticizers, perfumes, dyestuffs or any other adjuvant used in cosmetics, to the cosmetic compositions according to the invention.

A further subject of the present invention is a wavesetting process. According to this process, at least one wavesetting lotion as described above is applied to the hair which is then wound up on wavesetting rollers (15 to 30 mm diameter) and the head of hair is dried (temperature of the order of 25° to 55° C.).

The amount to be applied to the hair depends on the volume of the head of hair but is generally of the order of 10 to 100 cc, and preferably of the order of 20 to 50 cc.

The present invention has a further subject the crosslinked copolymers obtained by copolymerization of 43 to 16% by weight of methyl methacrylate, 54 to 25% by weight of dimethylamino-ethyl methacrylate, 12 to 52% by weight of octadecyl methacrylate and an amount of a crosslinking agent which does not exceed 0.15 part by weight per 100 parts of monomers.

The crosslinking agent is preferably ethylene glycol dimethacrylate, but other crosslinking agents with a similar structure can also be used.

The present invention has as a further subject the crosslinked copolymers mentioned above, the amine groups of which have been quaternised by means of a quaternising agent.

The copolymers used in the compositions according to the invention are produced according to the conventional process of polymerization, which consists of dissolving the various monomers in a solvent such as absolute ethanol, in the presence of a polymerization catalyst such as alpha,alpha'-azo-bis-isobutyronitrile or alpha,alpha'-azo-bis-isobutyronitrile hydrochloride and of heating them under nitrogen, while stirring, at a temperature of the order of 80° C.

The duration of heating is generally of the order of 6 to 24 hours.

The polymer is then isolated according to the conventional process.

If it is desired to produce the copolymers in the quaternised form, the quaternisation reaction can be carried out in situ by diluting the reaction mixture by adding a sufficient amount of the polymerization solvent and adding the quaternising agent in the desired amount to produce either partial quaternisation or complete quaternisation of the tertiary amine groups carried by the dimethylamino-ethyl methacrylate units of the copolymer.

The quaternisation reaction is generally exothermic, but, in order to make it go to completion, it is recommended to heat the mixture for a period of the order of 3 to 8 hours, at temperatures of about 50° to 80° C.

In order that the invention shall be better understood, preparation examples of copolymers as well as examples of cosmetic compositions based on these copolymers will now be described, by way of illustration but without implying any limitation.

EXAMPLES OF PREPARATIONS OF POLYMERS

EXAMPLE 1

2,667 of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer. The mixtue is stirred until the catalyst has dissolved and 1,080 g of methyl methacrylate, 1,220 g of octadecyl methacrylate, 1,700 g of dimethylamino-ethyl methacrylate and 6 g of ethylene glycol dimethyacrylate are introduced into it.

The mixture is heated at about 80° C. under nitrogen, and with stirring.

The solution gels but the mixture can still be stirred. After heating for 9 hours, the solution is diluted with 2,693 g of absolute ethanol and left to cool to 20° C. 1,360 g of freshly distilled dimethylsulphate are then introduced into it, drop by drop, via the dropping funnel. The temperature of the solution increases rapidly to the reflux temperature of ethanol and remains there until the end of the addition. Heating is then continued for 3 hours at about 80° C. and then the temperature is allowed to fall to 50° C. 1,300 g of solvent are then distilled under reduced pressure (30 mm Hg). Addition of 1,300 g of absolute ethanol and distillation of an equal amount of solvent is repeated three times, and then the solution is diluted with 1,300 g of absolute ethanol. An alcoholic solution of the quaternised crosslinked copolymer is thus obtained, with a yield of the order of 100%.

This copolymer has an average molecular weight of 1,200,000, dc/dn=0.120 (solvent AcOH/MeOH=80/20).

EXAMPLE II

Following the procedure of Example I, copolymerization of 1,624 g of dimethylamino-ethyl methacrylate, 1,712 g of octadecyl methacrylate, 664 g of methyl methacrylate and 6 g of of ethylene glycol dimethacrylate is carried out in 2,667 g of absolute ethyl alcohol, in the presence of 16 g of azo-bisisobutyronitrile.

At the end of copolymerization, the solution is diluted with 2,638 g of absolute ethyl alcohol and 1,305 g of dimethylsulphate are added so as to quaternise the tertiary amine group of the copolymer.

A quaternised crosslinked copolymer is thus obtained, with an average molecular weight of 1,200,000.

EXAMPLE III

Following the procedure of Example I, copolymerization of 1,204 g of methyl methacrylate, 908 g of octadecyl methacrylate, 1,888 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of polymerization, the solution is diluted with 2,793 g of absolute ethyl alcohol and 1,460 g of methyl methacrylate, 908 g of octadecyl methacrylate, 1,888 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of polymerization, the solution is diluted with 2,793 g of absolute ethyl alcohol and 1,460 g of dimethylsulphate are added in order to quaternise the tertiary amine groups of the dimethylamino-ethyl methacrylate units of the copolymer, to the extent of 100%.

A quaternised crosslinked copolymer is thus obtained, with an average molecular weight of 1,100,000.

EXAMPLE IV

Following the procedure of Example I, copolymerization of 1,368 g of methyl methacrylate, 488 g of octadecyl methacrylate, 2,144 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of copolymerization, the solution is diluted with 3,058 g of absolute ethyl alcohol and 1,725 g of dimethylsulphate are added in order to quaternise the tertiary amine groups of the dimethylamino-ethyl methacrylate units of the copolymer, to the extent of 100%.

A quaternised crosslinked copolymer is thus obtained, with an average molecular weight of 1,300,000.

EXAMPLE V

Following the procedure of Example I, copolymerization of 1,704 g of methyl methacrylate, 504 g of octadecyl methacrylate, 1,792 g of dimethylamino-ethyl methacrylate and 6 g of ethylene glycol dimethacrylate is carried out in 2,667 g of absolute ethanol, in the pesence of 16 g of azo-bis-isobutyronitrile.

At the end of the operation, the solution is diluted with 2,771 g of absolute ethyl alcohol and 1,438 g of dimethylsulphate are added in order to quaternise the tertiary amine amine groups of the dimethylamino-ethyl methacrylate units of the copolymer to the extent of 100%.

A quaternized crosslinked copolymer is thus obtained, with an average molecular weight of 1,500,000.

EXAMPLE VI

Following the procedure of Example I, copolymerization of 1,548 g of methyl methacrylate, 872 g of octadecyl methacrylate, 1,580 g of dimethylamino-ethyl methacrylate and 6 g of ethylene glycol dimethacrylate is carried out in 2,667 g of absolute ethyl alcohol, in the presence of 16 g of azo-bisisobutyronitrile.

At the end of the operation, the solution is diluted with 2,603 g of absolute ethyl alcohol and 1,270 of dimethylsulphate are added in order to quaternise the tertiary amine groups of the dimethylamino-ethyl methacrylate units of the copolymer, to the extent of 100%.

A quaternised crosslinked copolymer is thus obtained, with an average molecular weight of 1,400,000.

EXAMPLE VII

Following the procedure of Example I, copolymerization of 984 g of methyl methacrylate, 1,968 of octadecyl methacrylate, 1,048 g of dimethylamino-ethyl methacrylate and 6 g of ethylene glycol dimethacrylate is carried out in 2,667 g of absolute ethyl alcohol, in the presence of 16 g of azo-bisisobutyronitrile.

At the end of the operation, the solution is diluted with 2,178 g of absolute ethyl alcohol and 845 g of dimethylsulphate are added in order to quaternise the tertiary amine groups of the dimethylamino-ethyl methacrylate units of the copolymer, to the extent of 100%.

A quaternised crosslinked copolymer is thus obtained, with an average molecular weight of 1,000,000.

EXAMPLE VIII

A terpolymer according to the invention is prepared by following the procedure as stated in Example I above up to the quaternisation stage. The terpolymer (400 g) is then quaternised, not with dimethylsulphate, but with 135 g of 2-bromo-ethanol, carrying out the reaction at a temperature of 80° C. for 4 hours.

A polymer with a degree of quaternisation of 47% is obtained.

Its average molecular weight is 1,000,000.

EXAMPLE IX

The procedure given in Example VIII is followed, using 96 g of ethyl bromide instead of 2-bromo-ethanol, and carrying out the reaction at about 50° C. for 4 hours.

The polymer obtained, which has a degree of quaternisation of 75%, has an average molecular weight of 1,100,000.

EXAMPLE X

The procedure given in Example VIII is followed, using 78 g of β-propiolactone as the quaternising agent, and carrying out the reaction at 80° C. for 4 hours.

The polymer obtained is quaternised to the extent of 100% and it has an average molecular weight of 1,050,000.

EXAMPLE XI

Following the procedure given in Example VIII, a first quaternisation is carried out with 70 g of 2-bromo-ethanol, carrying out the reaction for 4 hours at 80° C. which enables a polymer with a degree of quaternisation of 25% to be obtained.

This polymer is subjected to a second quaternisation using 55 g of 1,3-propane-sulphone, also for 4 hours at 80° C. which gives an additional degree of quaternisation of 50%.

The polymer thus obtained, which is quaternised to the extent of 75% (25% by 2-bromo-ethanol and 50% by 1,3-propanesulphone has an average molecular weight of 1,100,000.

EXAMPLE XII

Following the procedure given in Example VIII, the terpolymer is quaternised using 108 g of 1N hydrochloric acid, carrying out the reaction for 4 hours at 80° C.

A copolymer, quaternised to the extent of 90%, which has an average molecular weight of 980,000, is obtained.

EXAMPLE XIII

Following the procedure given in Example VIII, a first quaternisation is carried out using 160 g of ethyl bromide and carrying out the reaction at 60° C. for 7 hours, after which a second quaternisation is carried out with 190 g of dimethyisalphate, carrying out the reaction for 4 hours at 80° C.

The polymer thus obtained is quaternised to the extent of 100% (46% by ethyl bromide and 54% by dimethylsulphate). It has an average molecular weight of 1,200,000.

EXAMPLE XIV

Following the procedure given in Example VIII, a first quaternisation is carried out using 160 g of 2-bromo-ethanol, carrying out the reaction for 7½ hours at 80° C. followed by a second quaternisation using 26.6 g of dimethylsulphate, carrying out the reaction for 4 hours at 80° C.

The polymer obtained has a degree of quaternisation of 100% (85% by 2-bromo-ethanol and 15% by dimethylsulphate). It has an average molecular weight of 1,200,000.

EXAMPLE XV

Following the procedure given in Example VIII, quaternisation is first carried out using 138 g of benzyl chloride, for 4 hours at 80° C. followed by a second quaternisation using 79 g of dimethylsulphate, carrying out the reaction for 4 hours at about 80° C.

The polymer obtained is quaternised to the extent of 100% (42% by benzyl chloride and 58% by dimethylsulphate). It has an average molecular weight of 1,200,000.

EXAMPLE XVI 2,667 g of absolute ethanol and 16 g of azo-bisisobutyronitrile are introduced into a 20 liter flask, equipped with a mechanical stirrer, a condenser which can also be used as a distillation column, a nitrogen inlet, a dropping funnel and a thermometer. The mixture is stirred until the catalyst has dissolved and 1,080 g of methyl methacrylate, 1,220 g of octadecyl methacrylate, 1,700 g of dimethylamino-ethyl methacrylate and 6 g of ethylene glycol dimethacrylate are introduced into it.

The mixture is heated at about 80° C. under nitrogen and with stirring.

The solution gels but the mixture can still be stirred. After heating for 9 hours, the solution is diluted with 2,693 g of absolute ethanol and left to cool to 20° C. The terpolymer is then precipitated by adding petroleum ether.

A terpolymer with an average molecular weight of 900,000 is thus obtained.

EXAMPLE XVII 2,667 g of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer.

The mixture is stirred until the catalyst has dissolved and 1,624 g of dimethylamino-ethyl methacrylate, 1,712 g of octadecyl methacrylate, 664 of methyl methacrylate and 6 g of ethylene glycol dimethacrylate are introduced into it.

The mixture is heated at a temperature of about 80° C. under nitrogen and with stirring.

The solution gels but the mixture can still be stirred. After heating for 9 hours, the solution is diluted with 2,693 g of absolute ethanol and is left to cool to 20° C.

The polymer obtained is purified by precipitation in petroleum ether.

It has an average molecular weight of 900,000.

EXAMPLES XVIII

Following the procedure given in Example XVII, copolymerization of 1,204 g of methyl methacrylate, 908 g of octadecyl methacrylate, 1,888 g of dimethylamino-ethyl methacrylate and 6 g of ethylene glycol dimethacrylate is carried out.

The polymer obtained has an average molecular weight of 800,000.

EXAMPLE XIX

Following the method of preparation described in Example XVII, copolymerization of 1,368 g of methyl methacrylate, 488 g of octadecyl methacrylate, 2,144 g of dimethylamino-ethyl methacrylate and 6 g of ethylene glycol dimethacrylate is carried out.

A polymer which has an average molecular weight of 900,000 is obtained.

EXAMPLE XX

Following the procedure given in Example XVII, copolymerization of 1,704 g of methyl methacrylate, 504 g of octadecyl methacrylate, 1,792 g of dimethylamino-ethyl methacrylate and 6 g of ethylene glycol dimethacrylate is carried out. A copolymer with an average molecular weight of 1,100,000 is obtained.

EXAMPLE XXI

Following the procedure given in Example XVII, copolymerization of 1,548 g of methyl methacrylate, 872 g of octadecyl methacrylate, 1,580 g of dimethylamino-ethyl methacrylate and 6 g of ethylene glycol dimethacrylate is carried out.

A copolymer which has an average molecular weight of 1,050,000 is obtained.

EXAMPLE XXII

Following the procedure of Example XVII, copolymerization of 984 g of methyl methacrylate, 1,968 g of octadecyl methacrylate, 1,048 g of dimethylamino-ethyl methacrylate and 6 g of ethylene glycol dimethacrylate is carried out.

A polymer with an average molecular weight of 850,000 is obtained.

EXAMPLE XXIII 81.66 g of methyl methacrylate, 90 g of octadecyl methacrylate, 128.34 g of dimethylamino-ethyl methacrylate, 1,200 g of absolute ethanol and 6 g of azo-bis-isobutyronitrile are introduced into a 2 liter flask, equipped with a mechanical stirrer, a condenser which can also be used as a distillation column, a nitrogen inlet, a dropping funnel and a thermometer.

The solution is stirred under nitrogen for 24 hours at a temperature of 80° C. and the polymer is left to cool; the polymer precipitates in petroleum ether in the form of a white powder.

The polymer obtained has an average molecular weight, M.W.=15,000, dc/dn=0.109.

Solvent: dioxane/methanol in the ratio 65/35

EXAMPLE XXIV 2,667 g of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer. The mixture is stirred until the catalyst had dissolved and 1,080 g of methyl methacrylate, 1,220 g of octadecyl methacrylate, 1,700 g of dimethylaminoethyl methacrylate and 3 g of ethylene glycol dimethacrylate are introduced into it.

The mixture is heated at 80° C. under nitrogen and with stirring.

The solution gels but the mixture can still be stirred. After heating for 9 hours, the solution is diluted with 2,693 g of absolute ethanol and left to cool to 20° C. 1,360 g of freshly distilled dimethylsulphate is then introduced into it, drop by drop, via the dropping funnel. The temperature of the solution increases rapidly to the reflux temperature of ethanol and remains there until the end of the addition. Heating is then continued for 3 hours at 80° C. and then the temperature is allowed to fall to 50° C. 1,300 g of solvent are then distilled under reduced pressure (30 mm Hg). Addition of 1,300 g of absolute ethanol and distillation of an equal amount of solvent is repeated three times, and then the solution is diluted with 1,300 g of absolute ethanol. An alcoholic solution of the quaternised crosslinked copolymer is thus obtained, with a yield of the order of 100%.

This copolymer has an average molecular weight of 600,000.

EXAMPLES OF COMPOSITIONS

EXAMPLE 1

A wavesetting lotion for hair is prepared by making up the following mixture:

| copolymer according to Example I | 2 g |
|---|---|
| absolute ethyl alcohol | 45 cc |
| water, q.s.p. | 100 cc |

Approximately 20 ml of this lotion are applied to hair which has been washed and towelled dry. The hair is then wound up on wavesetting rollers of 15 to 30 mm diameter and then dried by supplying heat externally.

The hair disentangles easily. The lacquering and the shine are excellent.

EXAMPLE 2

A wavesetting lotion for hair is prepared by making up the following mixture:

| copolymer according to Example II | 3 g |
|---|---|
| ethyl alcohol | 50 cc |
| water, q.s.p. | 100 cc |

After applying this lotion in accordance with the procedure of Example 1, excellent results are obtained, which are particularly outstanding with regard to the shine, the absence of stickiness and the easy of disentangling.

EXAMPLE 3

A wavesetting lotion for hair is prepared by making up the following mixture:

| copolymer according to Example VI | 1 g |
|---|---|
| isopropyl alcohol | 40 cc |
| water, q.s.p. | 100 cc |

10 to 30 ml of this lotion are applied to hair which has first been washed. The hair is wound up on wavesetting rollers and then dried under a hood at a temperature of 30° to 55° C. An excellent set is thus obtained. The hair is soft and shiny, and the set stays in very well even in the presence of moisture.

EXAMPLE 4

A wavesetting lotion is prepared by making up the following mixture:

| copolymer according to Example V | 1.5 g |
|---|---|
| isopropyl alcohol | 60 cc |
| perfume | 0.2 g |
| water, q.s.p. | 100 cc |

Approximately 20 ml of this lotion are applied to hair which has been washed and towelled dry. The hair is then wound up on wavesetting rollers of 15 to 30 mm diameter and is then dried by supplying heat externally.

The hair disentangles easily. The lacquering and the shine are excellent.

EXAMPLE 5

An aerosol lacquer for hair is prepared by making up the following mixture:

| copolymer according to Example XVI | 1.5 g |
|---|---|
| absolute ethyl alcohol, q.s.p. | 100 g |

33 g of this solution are then enclosed in an aerosol container in the presence of 66 g of a propellant gas consisting of a mixture of 61.5% of trichlorofluoromethane and 38.5% of dichlorodifluoromethane.

EXAMPLE 6

A lacquer for hair is prepared by making up the following mixture:

| copolymer according to Example XXIII | 2 g |
|---|---|
| absolute ethyl alcohol, q.s.p. | 100 g |

33 g of this mixture are placed in an aerosol container in the presence of 66 g of a propellant gas consisting of a mixture of 61.5% of trichlorofluoromethane and 38.5% of dichlorodifluoromethane.

EXAMPLE 7

An aerosol lacquer for hair is prepared by making up the following mixture:

| copolymer according to Example XXIV | 1.5 g |
|---|---|
| absolute ethyl alcohol, q.s.p. | 100 g |

33 g of this solution are introduced into an aerosol container in the presence of 66 g of a propellant gas consisting of a mixture of 61.5% of trichlorofluoromethane and 38.5% of dichlorodifluoromethane.

EXAMPLE 8

A wavesetting lotion for hair is prepared by making up the following mixture:

| | |
|---|---|
| copolymer according to Example XVIII | 1 g |
| isopropyl alcohol | 40 cc |
| water, q.s.p. | 100 cc |

10 to 30 ml of this lotion are applied to hair which has first been washed. The hair is wound up on wavesetting rollers and then dried under a hood at a temperature of 30° to 55° C. An excellent set is thus obtained. The hair is soft and shiny and the set stays in very well even in the presence of moisture.

EXAMPLE 9

A wavesetting lotion is prepared by making up the following mixture:

| | |
|---|---|
| copolymer according to Example XXI | 1.5 g |
| isopropyl alcohol | 60 cc |
| perfume | 0.2 g |
| water, q.s.p. | 100 cc |

After applying this lotion in accordance with the procedure of Example 8, excellent results are obtained, which are particularly outstanding with regard to the shine, the absence of stickiness and the ease of disentangling.

EXAMPLE 10

A wavesetting lotion for hair is prepared by making up the following mixture:

| | |
|---|---|
| copolymer according to Example XIV | 3 g |
| ethyl alcohol | 50 cc |
| water, q.s.p. | 100 cc |

This lotion enables hair to be set easily and above all gives it an excellent shine. The hair is soft to the touch and very easy to disentangle. This type of lotion is particularly suitable for sensitive or dry hair.

EXAMPLE 11

A wavesetting lotion for hair is prepared by making up the following mixture:

| | |
|---|---|
| copolymer according to Example VIII | 2 g |
| absolute ethyl alcohol | 45 cc |
| water, q.s.p. | 100 cc |

After applying this lotion in accordance with the procedure of Example 8, excellent results are obtained, which are particularly outstanding with regard to the shine, the absence of stickiness and the ease of disentangling.

EXAMPLE 12

A wavesetting lotion is prepared by making up the following mixture:

| | |
|---|---|
| copolymer according to Example XI | 1.5 g |
| isopropyl alcohol | 60 cc |
| perfume | 0.2 g |
| water, q.s.p. | 100 cc |

Approximately 20 ml of this lotion are applied to hair which has been washed and towelled dry. The hair is then wound up on wavesetting rollers of 15 to 30 mm diameter and is then dried by supplying heat externally. An excellent set is thus obtained; the hair is soft and shiny and the set stays in very well even in the presence of moisture.

EXAMPLE 13

A wavesetting lotion for hair is prepared by making up the following mixture:

| | |
|---|---|
| copolymer according to Example XII | 1 g |
| isopropyl alcohol | 40 cc |
| water, q.s.p. | 100 cc |

10 to 30 ml of this lotion are applied to hair which has first been washed. The hair is wound up on wavesetting rollers and then dried under a hood at a temperature of 30° to 55° C. An excellent set is thus obtained; the hair is solf and shiny and the set stays in very well even in the presence of moisture.

EXAMPLE 14

A wavesetting lotion for hair is prepared by making up the following mixture;

| | |
|---|---|
| copolymer according to Example XV | 3 g |
| ethyl alcohol | 50 cc |
| water, q.s.p. | 100 cc |

The lotion enables hair to be set very easily and above all gives it an excellent shine. The hair is soft to the touch and very easy to disentangle. This type of lotion is particularly suitable for sensitive or dry hair.

All parts listed herein are by weight unless indicated to the contrary.

What is claimed is:

1. An ethyl alcohol soluble cross-linked copolymer having tertiary amine groups and an average molecular weight of 10,000 and 1,500,000 and comprising (i) 16–43% by weight of methyl methacrylate, (ii) 25–54% by weight of dimethyl-amino-ethyl methacrylate, (iii) 12–52% by weight of octadecyl methacrylate and up to 0.15 part by weight of ethylene glycol dimethacrylate per 100 parts of (i)+(ii)+(iii), the average molecular weight being determined by the Light scattering method.

2. The copolymer of claim 1 wherein 47 to 100 percent of the tertiary amine groups are quaternized by a quaternizing agent selected from the group consisting of dimethyl sulphate, lower alkyl halides with 1 to 3 carbon atoms, 2-bromoethanol, β-propiolactone, 1,3-propane-sultone and benzyl chloride.

3. A process for preparing an ethyl alcohol soluble cross-linked copolymers having tertiary amine groups comprising: mixing (i) 16–43% by weight of methyl methacrylate, (ii) 25–54% by weight of dimethyl-amino-ethyl methacrylate, (iii) 12–52% by weight of octadecyl methacrylate and up to 0.15 parts by weight of ethylene glycol dimethacrylate per 100 parts of (i)+(ii)+(iii) and thereafter polymerizing in the presence of a polymerization catalyst at a temperature of about 80° C. until the average molecular weight is 10,000–1,500,000, the average molecular weight being determined by the Light scattering method.

4. The process of claim 3 wherein the (i) methyl methacrylate, (ii) dimethyl-amino-ethyl methacrylate, and (iii) octadecyl methacrylate, and the ethylene glycol methacrylate are dissolved in ethanol, and the polymerization is thereafter carried out for about 6–24 hours.

5. A process according to claim 4, wherein the polymerization is carried out under an inert atmosphere and at reflux temperature.

6. The process of claim 5, wherein the catalyst is azo-bis-isobutyronitrile.

* * * * *